US006869407B2

(12) United States Patent
Ein-Gal

(10) Patent No.: US 6,869,407 B2
(45) **Date of Patent: *Mar. 22, 2005**

(54) ACOUSTIC WAVE DEVICE

(76) Inventor: Moshe Ein-Gal, 30 Azar Street, Ramat Hasharon 47203 (IL)

(*) Notice: Subject to any disclaimer, the term of this patent is extended or adjusted under 35 U.S.C. 154(b) by 436 days.

This patent is subject to a terminal disclaimer.

(21) Appl. No.: 09/949,886

(22) Filed: Sep. 12, 2001

(65) Prior Publication Data

US 2003/0060738 A1 Mar. 27, 2003

(51) Int. Cl.[7] .............................................. A61B 17/22
(52) U.S. Cl. ................................ 601/2; 601/4; 600/439
(58) Field of Search ..................... 601/2, 3, 4; 600/437, 600/439; 606/427, 128

(56) References Cited

U.S. PATENT DOCUMENTS 3,942,531 A 3/1976 Hoff et al.
4,025,805 A * 5/1977 Coltman et al. ............ 310/335
4,539,989 A 9/1985 Forssmann et al.
4,674,505 A 6/1987 Pauli et al.
4,697,588 A * 10/1987 Reichenberger ................ 601/4
5,058,569 A 10/1991 Hassler et al.
5,174,280 A 12/1992 Gruenwald et al.
5,233,972 A * 8/1993 Rattner .......................... 601/4
6,685,657 B2 * 2/2004 Jones ............................ 601/2
2002/0002345 A1 * 1/2002 Marlinghaus .................. 601/2

* cited by examiner

*Primary Examiner*—Eleni Mantis Mercader
(74) *Attorney, Agent, or Firm*—Dekel Patent Ltd.; David Klein

(57) ABSTRACT

An acoustic wave device including an electrical element disposable on an outer contour of a support of an acoustic wave transducer, the outer contour having a non-cylindrical and non-flat shape, the electrical element being areally configured on the outer contour for radiating acoustic waves outwardly from the outer contour.

1 Claim, 2 Drawing Sheets

ACOUSTIC WAVE DEVICE

FIELD OF THE INVENTION

The present invention relates to generation and focusing of acoustic waves in general, and particularly to generation and focusing of acoustic waves with electromagnetic energy.

BACKGROUND OF THE INVENTION

Generation and focusing of acoustic waves (or shockwaves, the terms being used interchangeably throughout) for purposes of medical treatment such as stone fragmentation or orthopedic treatment are accomplished through a variety of methods. Each method incorporates acoustic wave generation and associated focusing apparatus. The prior art may be classified according to the geometry of the acoustic wave generation and associated focusing: point source and ellipsoidal reflector, planar source and acoustic lens, cylindrical source and parabolic reflector, and spherical source with no additional focusing. The prior art typically converts electrical energy into acoustic waves, such as by generating a strong pulse of an electric or magnetic field, usually by a capacitor discharge, and then converting the electromagnetic field into acoustic energy.

Point sources for the generation of acoustic waves in a lithotripter are described in various patents, such as U.S. Pat. Nos. 3,942,531 and 4,539,989, for example, the disclosures of which are incorporated herein by reference. A point source typically comprises electrohydraulic apparatus. Fast discharges of electrical energy between tips of closely spaced electrodes give rise to a sequence of spherical waves in a propagating liquid. The electrodes are arranged with respect to an ellipsoidal reflector, which has two focal points. The electrical energy is discharged at the first focus, and the waves are focused onto the second focus.

A planar source typically comprises electromagnetic apparatus. A thin circular membrane applies pressure to the propagation liquid by being jolted or repelled away from a planar coil. Fast discharges of electrical energy into the coil and the associated rapid changes in the magnetic field induce currents in the membrane, turning it into a magnet with a polarization opposite to that of the coil. The ensuing repulsions of the membrane, which is in close contact with the propagating liquid, generate the acoustic waves. U.S. Pat. No. 4,674,505, the disclosure of which is incorporated herein by reference, describes an example of such a planar source with an associated acoustic lens.

Apparatus incorporating a cylindrical source uses an electromagnetic approach similar to that used for the planar source. A coil is mounted on a cylindrical support and a cylindrical membrane, being pushed or repelled radially, gives rise to outwardly propagating cylindrical waves. A parabolic reflector focuses the waves into a point on the cylindrical axis of the system. Cylindrical sources enable using an in-line ultrasonic probe for imaging the focal area. Examples of cylindrical sources are described in U.S. Pat. No. 5,058,569 to Hasssler et al., assigned to Siemens Aktiengesellschaft (Munich, Germany) and U.S. Pat. No. 5,174,280 to Gruenwald et al., assigned to Dornier Medizintechnik GmbH (Germering, Germany), the disclosures of which are incorporated herein by reference.

Spherical waves are generated by an array of piezoelectric transducers or by an electromagnetic approach with a spherical membrane being repulsed inwardly into the propagating liquid. No further focusing is required. Spherical sources are mentioned in the background of U.S. Pat. No. 5,174,280.

Each of the prior art acoustic wave generation and focusing apparatus has limitations. Acoustic wave generators generate shocks at a rate of one or two shocks per second, whereas extracorporeal shockwave treatment (ESWT) typically requires thousands of shocks per treatment. The electrohydraulic approach suffers from the disadvantages of non-uniform discharges, pain and high noise level. The electromagnetic planar approach suffers from the disadvantages of high cost and complexity in manufacturing the coil and lens assembly. Acoustic lenses for planar sources are fragile and non-effective for large apertures. In addition to the complexity of manufacturing electromagnetic cylindrical sources, the parabolic reflector is not highly efficient because the source is in the way of reflected waves adjacent thereto. The piezo-electric array is expensive to manufacture, and it is difficult to obtain high-level, well-distributed intensities. The array requires a relatively large aperture that prevents access for x-ray imaging of the focal area.

SUMMARY OF THE INVENTION

The present invention seeks to provide an improved acoustic wave device that includes a truncated conical acoustic wave transducer. A modified parabolic reflector may be arranged with respect to the conical transducer so as to focus acoustic waves emanating therefrom towards a focal point, which is the apex of the conical transducer.

Acoustic waves may be generated by an area transducer, such as a truncated conical area transducer. For example, a coil may repel or vibrate a conical membrane to produce acoustic waves. In another example, a conducting surface electrode may be mounted on the outer contour of the conical transducer. A perforated insulator may at least partially cover the surface electrode, and may be sandwiched between the surface electrode and a return electrode. A multiplicity of electrical currents may flow through the perforations of the perforated insulator, which give rise to point sources of ultrasonic energy in the form of spherical waves emanating from the perforations.

Acoustic waves may also be generated by means of a force generator mounted in juxtaposition to the base of the conical transducer. The force generator transmits a force that has two vector components, one vector component generally along the contour of the conical transducer and another vector component generally perpendicularly outwards from the outer contour of the conical transducer. The force component perpendicular to the outer contour generates conical acoustic waves emanating outwards from the outer contour of the conical transducer.

There is thus provided in accordance with a preferred embodiment of the invention an acoustic wave device including an acoustic wave device including an acoustic wave transducer including a support constructed of an electrically conducting material, and one or more coil segments wound about the support, wherein an electrical current passing through the coil segments induces an induced current in the support, the induced current generating an electromagnetic force that repels the coil segments outwards from the support.

In accordance with a preferred embodiment of the invention the support has a non-cylindrical shape, such as a truncated conical shape.

Further in accordance with a preferred embodiment of the invention the coil segments are electrically connected in parallel.

Still further in accordance with a preferred embodiment of the invention a voltage drop across each of the coil segments does not exceed 2000 volts.

There is also provided in accordance with a preferred embodiment of the invention an acoustic wave device including an electrical element disposable on an outer contour of a support of an acoustic wave transducer, the outer contour having a non-cylindrical and non-flat shape, the electrical element being areally configured on the outer contour for radiating acoustic waves outwardly from the outer contour.

In accordance with a preferred embodiment of the invention the electrical element includes a coil mountable on an outer contour of a support of an acoustic wave transducer and a membrane shaped to conform to the outer contour, wherein the coil is adapted to move the membrane outwards from the support.

Further in accordance with a preferred embodiment of the invention the electrical element includes a coil mountable on an outer contour of a support of an acoustic wave transducer and a magnet disposable on the support adapted to generate a magnetic field that repels the coil outwards from the support.

Still further in accordance with a preferred embodiment of the invention the electrical element includes a conducting surface electrode mountable on the outer contour, a perforated insulator that at least partially covers the conducting surface electrode, and a return electrode disposed on a side of the perforated insulator opposite to the conducting surface electrode.

There is also provided in accordance with a preferred embodiment of the invention an acoustic wave device including an electrical element disposable on an outer contour of a support of an acoustic wave transducer, the electrical element being areally configured on the outer contour for radiating acoustic waves outwardly from the outer contour, and a magnet disposable on the support adapted to generate a magnetic field that repels the electrical element outwards from the support. The electrical element may be a coil, for example. The support may be non-cylindrical and non-flat.

There is also provided in accordance with a preferred embodiment of the invention an acoustic wave device including an electrical element disposable on an outer contour of a support of an acoustic wave transducer, the electrical element being areally configured on the outer contour for radiating acoustic waves outwardly from the outer contour, and a perforated insulator that at least partially covers the electrical element. The support may be non-cylindrical and non-flat.

In accordance with a preferred embodiment of the invention the electrical element includes a conducting surface electrode mountable on the outer contour, and a return electrode disposed on a side of the perforated insulator opposite to the conducting surface electrode.

BRIEF DESCRIPTION OF THE DRAWINGS

The present invention will be understood and appreciated more fully from the following detailed description taken in conjunction with the drawings in which.

DETAILED DESCRIPTION OF A PREFERRED EMBODIMENT

Figure 1:
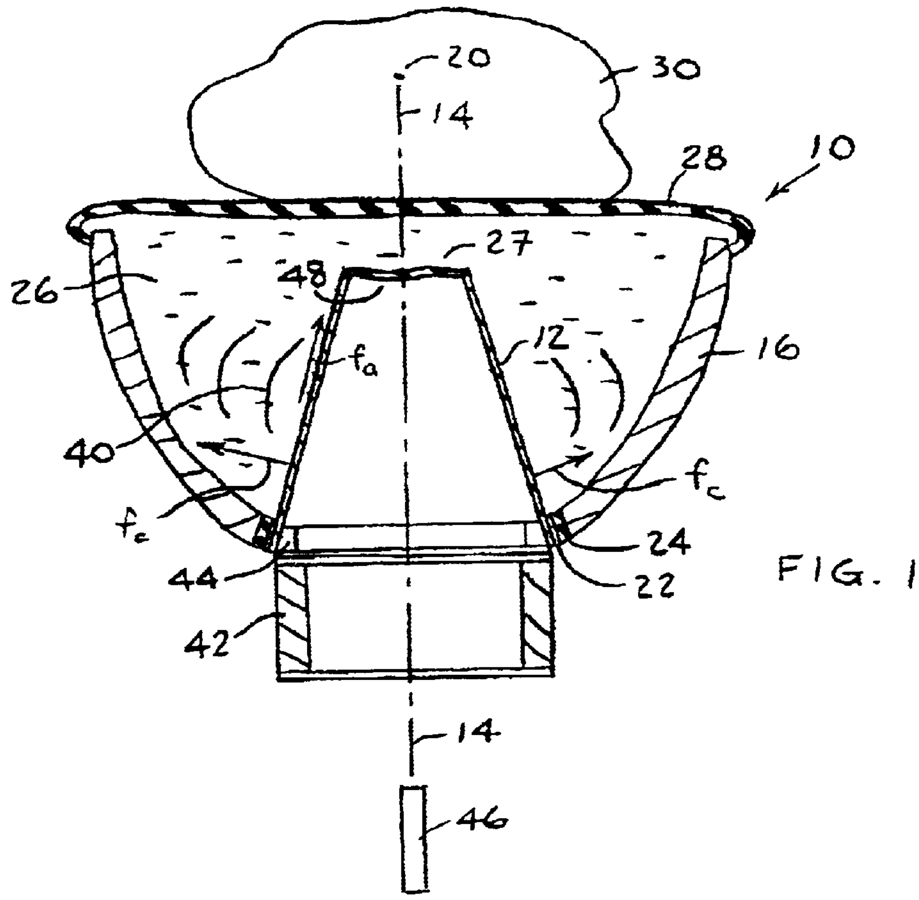
FIG. 1 is a simplified pictorial illustration of an acoustic wave device, constructed and operative in accordance with a preferred embodiment of the invention.

Reference is now made to FIG. 1 which illustrates an acoustic wave device 10, constructed and operative in accordance with a preferred embodiment of the present invention.

In the illustrated embodiment, acoustic wave device 10 includes an acoustic wave transducer 12 shaped like a cone, most preferably a truncated cone, with an axis of symmetry 14. An at least partially parabolic reflector 16 is arranged with respect to transducer 12 so as to focus an acoustic wave emanating from transducer 12. However, it is noted that the present invention is not limited to a cone-shaped acoustic wave device, and may be carried out with other shapes as well, such as but not limited to, cylindrical acoustic wave devices.

The inner volume of reflector 16 may be filled with a propagation liquid 26, and an open end 48 of transducer 12 may be covered with a membrane 27 in order to seal the inside of the conical transducer 12 from ingress therein of propagation liquid 26. The end face of reflector 16 may be covered with another membrane 28. Acoustic wave device 10 may be placed against or near a target 30, which it is desired to treat. Acoustic waves generated by transducer 12 may propagate towards focal point 20, located in target 30, via propagating liquid 26 and through membrane 28. The acoustic waves may be produced in a variety of manners, as is described hereinbelow with reference to FIGS. 2–5.

Figure 2:
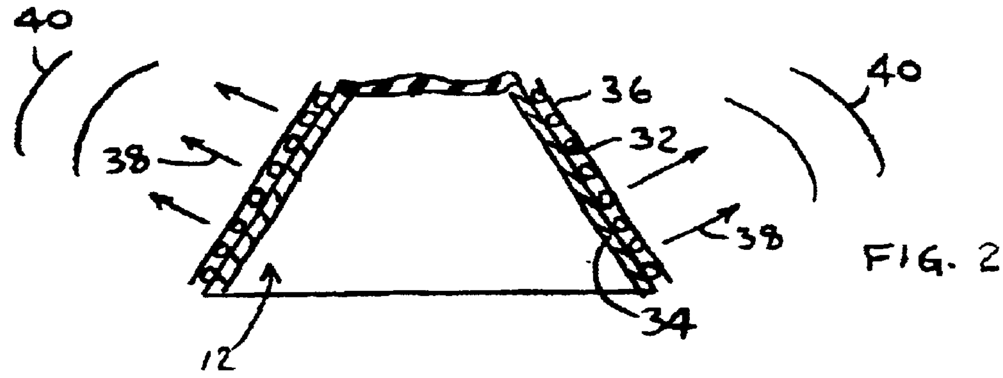
FIG. 2 is a simplified sectional illustration of an area transducer that may be used to generate acoustic waves, with a coil and membrane arrangement, in accordance with a preferred embodiment of the invention.

Reference is now made to FIG. 2, which illustrates an area transducer that may be used to generate the acoustic waves, in accordance with a preferred embodiment of the invention. The area transducer comprises an electrical element 32, such as a coil, mounted on a truncated conical support 34 of transducer 12. A membrane 36 is shaped to conform to the conical outer contour of support 34 and is disposed on electrical element 32. The coil is adapted to move (e.g., repel or vibrate) membrane 36 outwards from truncated conical support 34, generally in the direction of arrows 38, so as to propagate acoustic waves 40 in a direction outwards from the contour of transducer 12. As mentioned hereinabove, acoustic waves 40 reflect off reflector 16 and propagate towards focal point 20 through membrane 28 (FIG. 1).

Reference is now made again to FIG. 1. Another way of generating acoustic waves in the present invention is by means of a force generator 42 mounted in juxtaposition to the base of conical transducer 12. Force generator 42 may be coupled to transducer 12 by means of a mechanical coupler 44. Force generator 42 is adapted to transmit a force generally along axis 14, which force is transmitted to the outer contour of transducer 12, thereby giving rise to acoustic waves 40. Specifically, the force has two vector components, one vector component $f_a$ generally along the contour of conical transducer 12 and another vector component $f_c$ generally perpendicularly outwards from the outer contour of transducer 12. The force component $f_c$ generates conical acoustic waves 40 emanating outwards from the outer contour of transducer 12, as seen in FIG. 1. The direction of the force $f_a$ (towards the cone apex or away from it) determines the polarity of the acoustic waves 40 (expanding or retracting). The intensity of the waves is proportional to the sine of the cone angle.

The force generator 42 may be any suitable device for generating force impulses, such as, but not limited to, a reciprocating hammer device, a "flying" mass accelerator adapted to cause a mass to impinge on transducer 12, an explosive, an underwater electrical discharge unit, an electromagnetic actuator, a piezoelectric actuator, a pneumatic actuator or a hydraulic actuator, for example.

Transducer 12 is preferably hollow so that imaging apparatus 46, such as an in-line ultrasonic probe, may be used to image the focal area, such as via the open truncated end 48 of transducer 12.

Figure 3A:
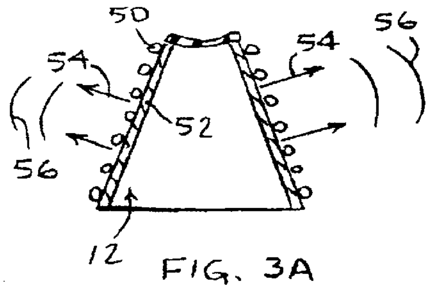
FIG. 3A is a simplified sectional illustration of an area transducer that may be used to generate acoustic waves, with coil segments, in accordance with a preferred embodiment of the invention.
Figure 3B:
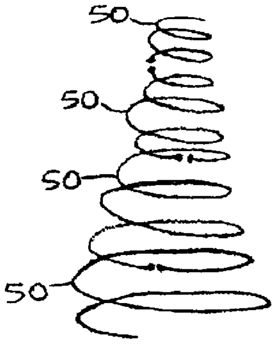
FIG. 3B is a simplified illustration of the coil segments of the transducer of FIG. 3A.

Reference is now made to FIGS. 3A and 3B, which illustrate an area transducer that may be used to generate acoustic waves, with one or more coil segments 50, in accordance with a preferred embodiment of the invention. Coil segments 50 are wound about a non-cylindrical and non-flat support 52 of the acoustic wave transducer. Support 52 is illustrated as having a truncated conical shape, but may have other shapes as well that are non-cylindrical and non-flat. Conical support 52 is preferably constructed of an electrically conducting material, such as a conductive metal. The coil segments 50 may be made from wire, such as but not limited to, having a diameter of 0.2 mm. Electrical current passing through coil segments 50 induces an induced current in conical support 52, which generates an electromagnetic force that repels coil segments 50 outwards from conical support 52, generally in the direction of arrows 54, so as to propagate acoustic waves 56 in a direction outwards from the contour of conical support 52. As mentioned similarly hereinabove, acoustic waves 56 reflect off reflector 16 and propagate towards focal point 20 through membrane 28 (FIG. 1).

Figure 3C:
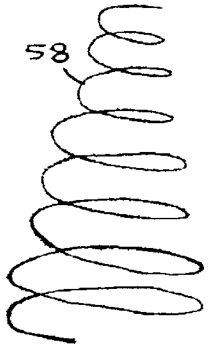
FIG. 3C PRIOR ART
FIG. 3C is a simplified illustration of a prior art coil.

In the prior art, as shown in FIG. 3C, a long, continuous coil 58 is wound on the coil support (cylindrical in the prior art). This necessitates using high voltage, typically in the order of 20,000 volts, to generate the electromotive repelling force to repel the coil windings from the transducer base to generate the acoustic waves. In contrast, in accordance with a preferred embodiment of the invention, coil segments 50 are much shorter in length, such as but not limited to, lengths with a voltage drop of only 2000 volts. The segments 50 may be electrically connected in parallel. This is a significant advantage over the prior art, because the coil segments 50 of the present invention may enable achieving the same high currents by using a suitable low voltage power supply and transformer (not shown).

Figure 4:
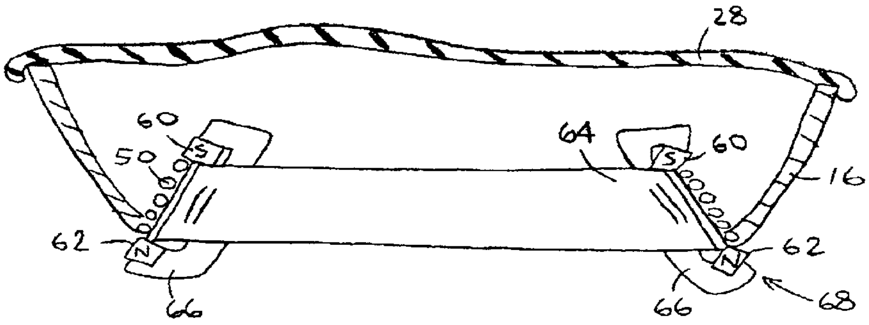
FIG. 4 is a simplified sectional illustration of an area transducer that may be used to generate acoustic waves with electromagnetic force, in accordance with a preferred embodiment of the invention.

Reference is now made to FIG. 4, which illustrates an area transducer that may be used to generate acoustic waves with a repelling electromagnetic force, in accordance with a preferred embodiment of the invention. This embodiment may also use coil segments 50 as in the embodiment of FIGS. 3A and 3B. However, in the embodiment of FIG. 4, a magnetic field is set up by a magnet disposed about the conical transducer. For example, a pair of magnets 60 and 62 may be placed at ends of a truncated conical support 64, connected by a magnetic yoke 66 so as to form a conical magnet 68. Magnet 68 is preferably constructed of a material with a high magnetic permeability, such as but not limited to, samarium cobalt. Alternatively, the magnetic field may be set up by use of coils (not shown). Conical support 64 is preferably constructed of an electrically conducting material, such as a conductive metal. In accordance with electromagnetic laws, a repelling force f is generated by the magnetic field B of magnet 68 and the electrical current i of coil segments 50, in accordance with the formula:

$f=iLB$, wherein L is the length of the coil, or the total length of the coil segments.

As described similarly previously, the force f repels coil segments 50 outwards from conical support 64 so as to propagate acoustic waves in a direction outwards from the contour of conical support 64. As mentioned similarly hereinabove, the acoustic waves reflect off reflector 16 and propagate towards focal point 20 through membrane 28 (FIG. 1).

As described in the background, except for a point source, all other prior art methods for generating acoustic waves incorporate area conversion of electrical energy to planar, cylindrical or spherical acoustic waves close to the interface between the transducer and the propagation liquid. In contrast to the prior art, the present invention describes a device for generating ultrasonic waves emanating from a surface of arbitrary shape, as is now described with reference to FIG. 5.

Figure 5:
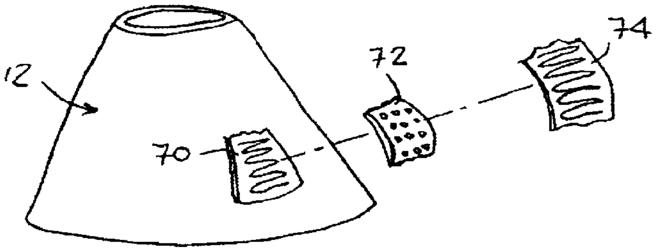
FIG. 5 is a simplified exploded illustration of another area transducer that may be used to generate the acoustic waves, wherein a multiplicity of electrical currents flow through perforations of a perforated insulator placed intermediate a surface electrode and a return electrode, in accordance with another preferred embodiment of the invention.

Reference is now made to FIG. 5, which illustrates another area transducer that may be used to generate the acoustic waves, in accordance with another preferred embodiment of the invention. In this embodiment, a conducting surface electrode 70 is mounted on the outer contour of transducer 12. A perforated insulator 72 at least partially covers the surface electrode 70. A return electrode 74 is disposed on a side of perforated insulator 72 opposite to the surface electrode 70. A multiplicity of electrical currents may flow through the perforations or holes of perforated insulator 72, once an electric field is established between the surface electrode 70 and the return electrode 74, e.g., by applying high voltage to the surface electrode 70 and grounding the return electrode 74. Each current, provided sufficient current density and duration, gives rise to a point source of ultrasonic energy in the form of a spherical wave emanating from the respective hole. The multiplicity of individual spherical waves, provided the perforation distribution is adequate in density and uniformity, forms a wave whose front is generally parallel to the surface of the surface electrode 70.

It will be appreciated by person skilled in the art, that the present invention is not limited by what has been particularly shown and described herein above. Rather the scope of the present invention is defined only by the claims that follow:

I claim:

1. An acoustic wave device comprising:

an acoustic wave transducer comprising a non-cylindrical, non-ring shaped and non-flat support constructed of an electrically conducting material wherein said support has a truncated conical shape;

a plurality of short coil segments electrically connected in parallel wound about said support, wherein an electrical current passing through said short coil segments induces an induced current in said truncated conical support, said induced current generating an electromagnetic force that repel said short coil segments outwards from said support; and a membrane shaped to conform to the outer contour of said truncated conical support and said plurality of short coil segments, wherein said plurality of short coil segments are adapted to move said membrane outwards from said truncated conical support.

* * * * *